United States Patent [19]
Arison et al.

[11] Patent Number: 5,952,347
[45] Date of Patent: Sep. 14, 1999

[54] QUINOLINE LEUKOTRIENE ANTAGONISTS

[75] Inventors: Byron H. Arison, Watchung, N.J.; Thomas A. Baillie, East Greenville; Suresh K. Balani, Hatfield, both of Pa.; Claude Dufresne, Quebec, Canada

[73] Assignee: Merck & Co., Inc., Rahway, N.J.

[21] Appl. No.: 09/037,949

[22] Filed: Mar. 10, 1998

Related U.S. Application Data

[60] Provisional application No. 60/040,413, Mar. 13, 1997.

[51] Int. Cl.$^6$ ........................ A61K 31/47; C07D 215/36; C07D 215/14
[52] U.S. Cl. ............................................ 514/311; 546/174
[58] Field of Search .............................. 546/174; 514/311

[56] References Cited

U.S. PATENT DOCUMENTS

| | | | |
|---|---|---|---|
| 4,918,081 | 4/1990 | Huang et al. | 514/311 |
| 4,920,130 | 4/1990 | Huang et al. | 514/311 |
| 5,104,882 | 4/1992 | Young et al. | 514/311 |
| 5,565,473 | 10/1996 | Belley | 514/313 |

*Primary Examiner*—Evelyn Mei Huang
*Attorney, Agent, or Firm*—Mollie M. Yang; David L. Rose

[57] ABSTRACT

Compounds of Formula I:

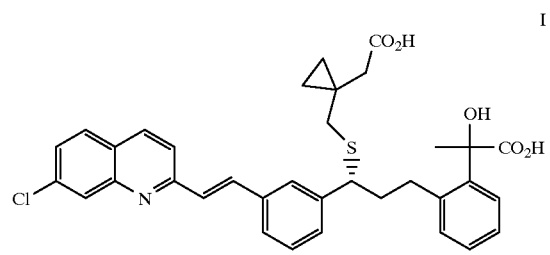

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

6 Claims, No Drawings

QUINOLINE LEUKOTRIENE ANTAGONISTS

CROSS REFERENCE TO RELATED APPLICATIONS

This application is based on, and claims priority from, provisional application 60/040,413 filed on Mar. 13, 1997.

BACKGROUND OF THE INVENTION

U.S. Pat. No. 5,565,473 discloses the compound of the formula (a):

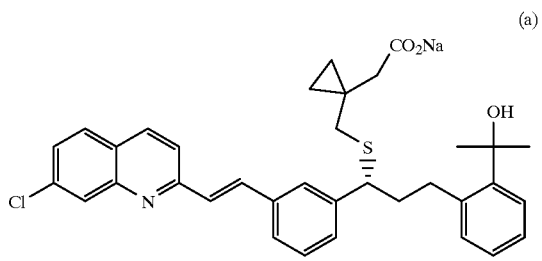

(a)

now generally known as montelukast sodium. Montelukast sodium is a leukotriene antagonist and is currently undergoing clinical trials for the treatment of chronic asthma.

PCT Published Application WO96/40638 published Dec. 19, 1996 discloses compounds of formulae (b) and (c), and their individual optical isomers, which are metabolites of montelukast sodium and are themselves leukotriene antagonists.

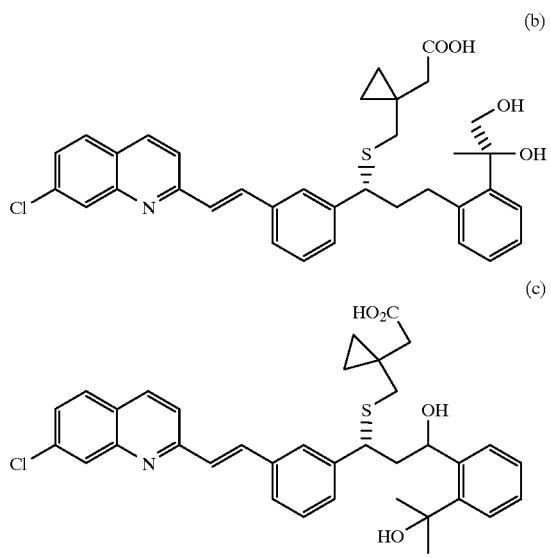

SUMMARY OF THE INVENTION

The present invention relates to quinoline diacid compounds having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

DETAILED DESCRIPTION OF THE INVENTION

The present invention provides compounds of formula I:

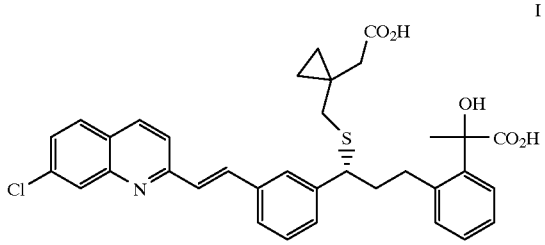

I and the individual optical isomers thereof; or a pharmaceutically acceptable derivative thereof.

In one embodiment there is provided a compound of formula I which is isolated and purified, i.e. a compound of formula I which is substantially free of other metabolic products of montelukast sodium.

In another aspect the present invention provides a method for preventing the actions of leukotrienes in mammals which comprises administering to said mammal a therapeutically effective amount of a compound of formula I.

In another aspect the present invention provides a method for the prevention and treatment of asthma, allergies or inflammation in a mammal which comprises administering to said mammal a therapeutically effective amount of a compound of formula I.

In yet another aspect the present invention provides a pharmaceutical composition which comprises a compound of formula I and a pharmaceutically acceptable carrier.

Another aspect of the present invention provides processes for the preparation of a compound of formula I.

Compounds described herein contain two asymmetric centers and may thus give rise to diastereomers and optical isomers. The present invention is meant to comprehend such possible diastereomers individually or as diastereomeric mixture, as well as their racemic and resolved, enantiomerically pure forms and pharmaceutically acceptable derivatives thereof.

The pharmaceutical compositions of the present invention comprise a compound of Formula I as an active ingredient or a pharmaceutically acceptable derivative thereof, and may also contain a pharmaceutically acceptable carrier and optionally other therapeutic ingredients. The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "pharmaceutically acceptable derivative" refers to any pharmaceutically acceptable salt, ester, ether, amide, or macromolecular prodrugs, or combination thereof. The invention also includes any other compounds which, upon administration to the recipient, is capable of providing (directly or indirectly) a compound of this invention.

Pharmaceutically acceptable salts include salts prepared from pharmaceutically acceptable non-toxic inorganic and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, dicyclohexylamine, polyamine resins, procaine, purines, theobromine, triethylamine, trimethylamine, tripropylamine, tromethamine, and the like.

Pharmaceutically acceptable esters include those formed from a hydroxy group of a compound of formula I and an organic acid (or an acylating equivalent thereof), such as acetate, adipate, alginate, aspartate, benzoate, benzenesulfonate, butyrate, citrate, camphorate, camphorsulfonate, cyclopentanepropidnate, glucoheptanoate, glycerophosphate, gluconate, dodecylsulfate, ethanesulfonate, fumarate, heptanoate, hexanoate 2-hydroxyethanesulfonate, lactate, maleate, methanesulfonate, 2-naphthanlenesulfonate, nicotinate, oxalate, pamoate, pectinate, picrate, pivalate, succinate, tartrate, tosylate, imidazole-1-carboxylate, phenylpropionate, phenoxyacetate, palmitate, laurate, adamantoate, stearate, octanoate, cycloalkylcarboxylate, decanoate, merystylate, phthalate, hexanoate, carbamate, adenosine-5'-carboxylate, pivaloyloxymethylate, in the substituted or non-substituted forms, and the like; or those formed from a carboxyl group of a compound of formula I and an alcohol such as a $C_1$–$C_4$ alkanol, or other alcohols commonly known in the art to form ester prodrugs. Pharmaceutically acceptable esters also include those formed from Formula I with inorganic acids such as, but not limited to, sufates, phosphates, carbonates, or conjugates of Formula I with glutathione, glucuronic acid, sugars (like glucose), and bile acids (like taurine), etc.

Pharmaceutically acceptable ethers are those which would readily occur to the skilled artisan, and include, for example, methyl through pentyl, cycloalkyl, methoxymethyl, 3'-hydroxypropyl, benzyl, allyl, anisylidene, ethoxyethyledene, tetrahydropyranyl, silyl ethers.

Pharmaceutically acceptable amides are those which would readily occur to the skilled artisan, and include, for example, $C_1$–$C_4$ amides.

Compounds of Formula I could also be used as a macromolecular prodrug involving Formula I bound covalently of reversibly to mono- or polyclonal antibodies, and other macromolecules, such as polyvinylic, polyacrylic, polysaccharidic, and poly-(a-amino acid) backbones, and dextran, soluble starch or hydroxyalkylstarch-based ester prodrugs, and insulin.

It will be understood that in the discussion of methods of treatment which follows, references to the compounds of Formula I are meant to also include the pharmaceutically acceptable derivatives.

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, myocardial ischemia, hypertension, platelet aggregation, and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia, and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg)

of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, skin patches, sustained release systems and the like.

The pharmaceutical compositions of the present invention comprise a compound of Formula I as an active ingredient or a pharmaceutically acceptable derivative thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |

| -continued | |
|---|---|
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:

(1) propionic acid derivatives;
(2) acetic acid derivatives;
(3) fenamic acid derivatives;
(4) oxicams; and
(5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free $-CH(CH_3)COOH$ or $-CH_2CH_2COOH$ group (which optionally can be in the form of a pharmaceutically acceptable salt group, e.g., $-CH(CH_3)COO^-Na^+$ or $-CH_2CH_2COO^-Na^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free $-CH_2COOH$ group (which optionally can be in the form of a pharmaceutically acceptable salt group, e.g. $-CH_2COO^-Na^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

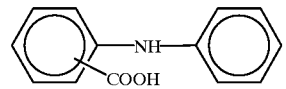

which can bear a variety of substituents and in which the free $-COOH$ group can be in the form of a pharmaceutically acceptable salt group, e.g., $-COO^-Na^+$.

The biphenylcarboxylic acid derivatives which can be used comprise: diflunisal and flufenisal. Structurally related biphenyl-carboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

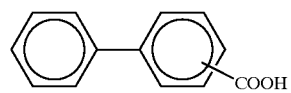

which can bear a variety of substituents and in which the free $-COOH$ group can be in the form of a pharmaceutically acceptable salt group, e.g., $-COO^-Na^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

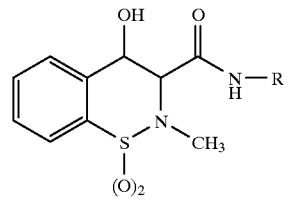

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058, 785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethyl-histidine, described in U.S. Pat. No. 4,325, 961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine, loratadine and like compounds, such as those disclosed in U.S. Pat. Nos. 4,283,408; 4,362,736; and 4,394, 508. The pharmaceutical compositions may also contain a $K^+/H^+$ ATPase inhibitor such as omeprazole, disclosed in U.S. Pat. No. 4,255,431, and the like. Compounds of Formula I may also be usefully combined with mast cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Preparation

Compounds of formula I are biliary metabolites of montelukast sodium. Therefore, they can be isolated and purified from bile of individuals who have ingested montelukast sodium, using methodologies that are well known in the art, such as chromatography.

Alternatively, compounds of the present invention can be prepared according to the following chemical methods dscribed in Schemes 1 and 2.

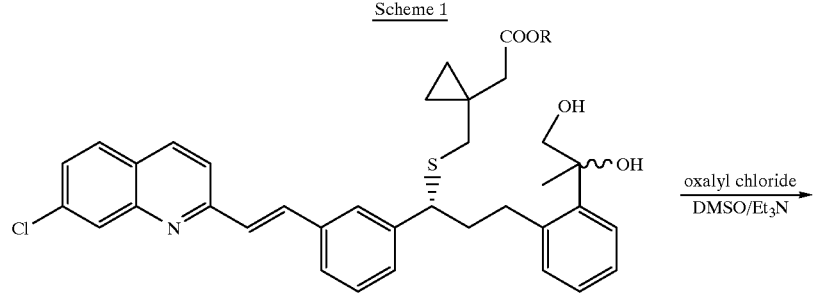

Scheme 1

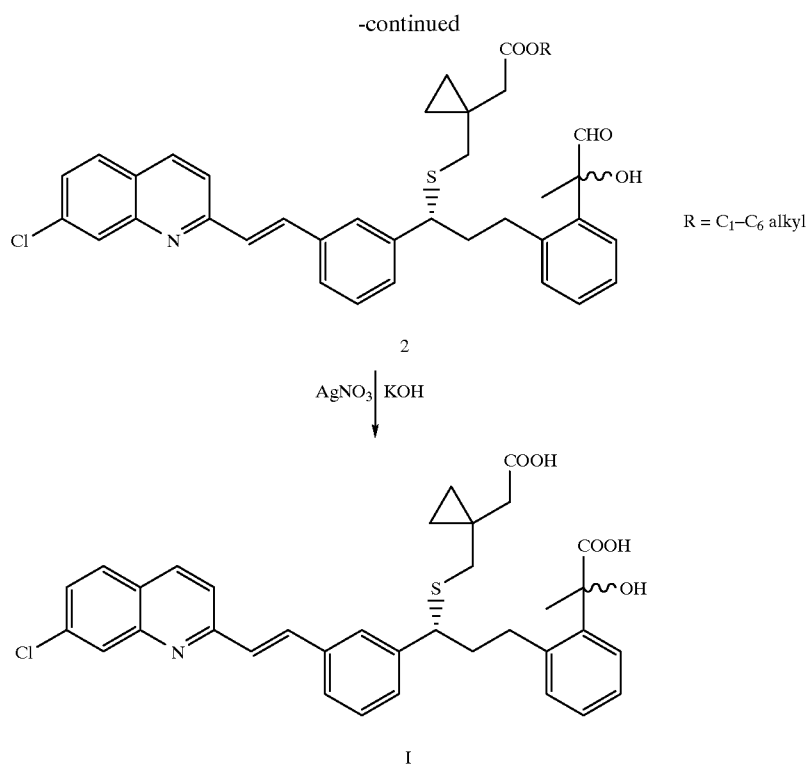

In Scheme 1, the diol ester 1 is oxidized to the corresponding aldehyde 2 using an oxidant, for example, dimethylsulfoxide and electrophile such as oxalyl chloride. The reaction is carried out in an inert organic solvent such as methylene chloride, and at temperature below 0° C., for example at about −60° C. Diol 1 is a known compound, and may be prepared according to the method described in *J. Org. Chem.*, 1996, 61:8518–8525.

Further oxidation of the aldehyde 2 to the diacid I is accomplished with silver nitrate and a base such as potassium hydroxide. The oxidation is conveniently carried out at room temperature in ethanol.

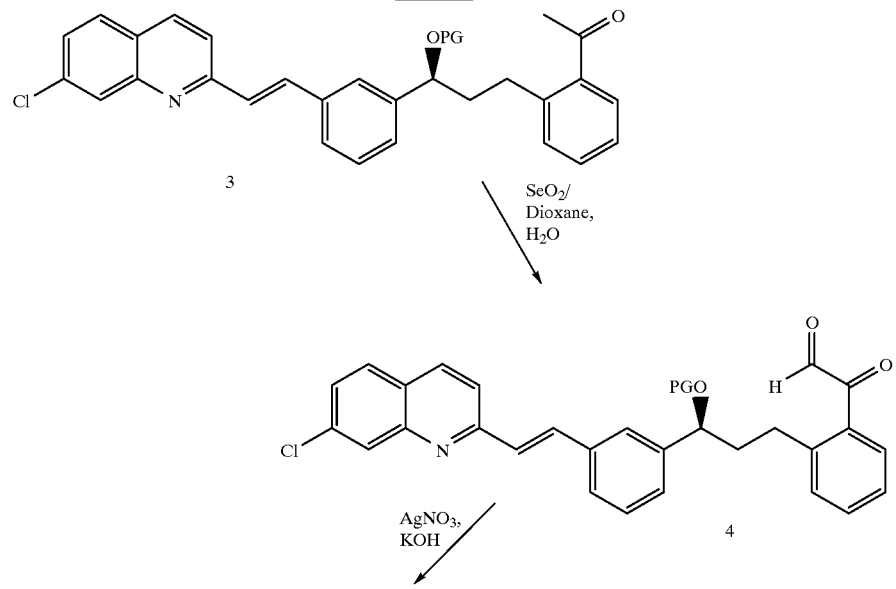

-continued
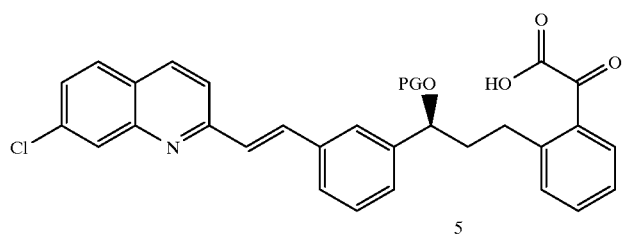
oxalyl chloride
8-phenyl menthol
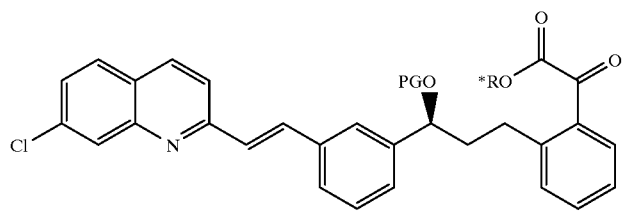
R* = 8-phenylmentholate
PG = hydroxy protecting group
6 →[1. MeMgBr][2. —PG]
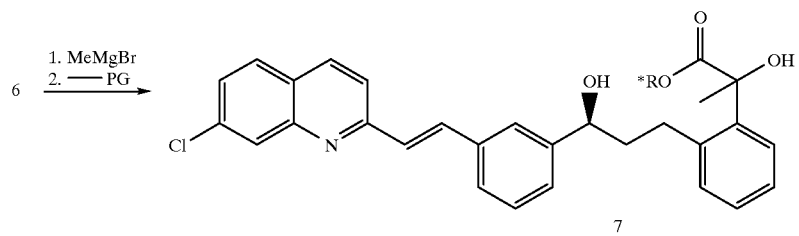
(major and minor isomers separate
1. MsCl
2. HS~~CO2H~~ (cyclopropyl)
   nBuLi
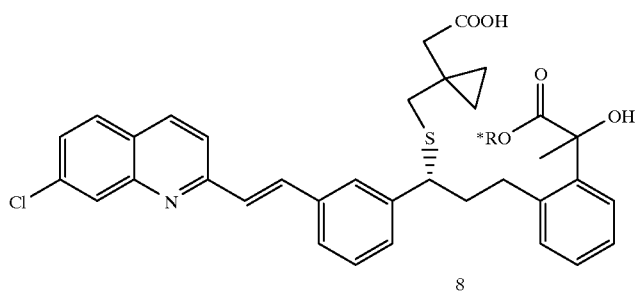
↓ LiOH/EtOH -continued

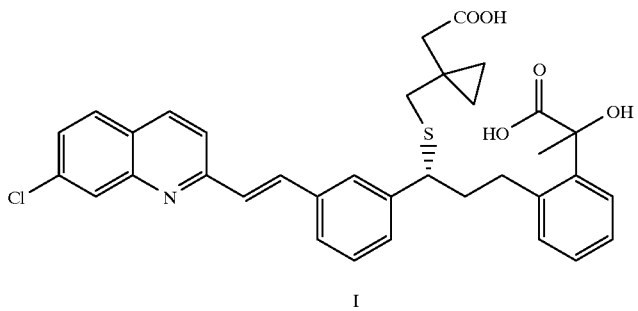

I

In Scheme 2, the protected hydroxy ketone 3 is oxidized with selenium dioxide to provide the corresponding a-ketoaldehyde 4. The hydroxy protecting group may be for example the t-butyldimethylsilyl group. Hydroxy ketone 3 may be prepared according to the method described in *J. Org. Chem.*, 1993, 58:3731–3735).

The a-ketoaldehyde 4 is oxidized to the corresponding a-ketocarboxylic acid 5, which is then derivatized to its 8-phenylmenthol ester 6. Treatment of 6 with methyl magnesium bromide followed by deprotection provides diol ester 7 as a diastereomeric mixture. The individual diastereomers are separated using chromatography. Each diastereomer is separately used to prepare the individual diastereomers of formula I.

Thus, the secondary hydroxyl group of 7 is mesylated, and then reacted with the dianion of 1-mercaptomethylcyclopropaneacetic acid, generated in situ with n-butyl lithium, to provide the ester compound 8. Hydrolysis of 8 with a base such as lithium hydroxide yields the desired diacid of formula I.

Assays for Determining Biological Activity

The leukotriene antagonist properties of the compounds of the present invention are evaluated using the following assays:

1. [$^3$H]LTD$_4$ Receptor Binding Assay in DMSO-differentiated U937 Cells (a human monocytic cell line);
2. [$^3$H]LTD4 Receptor Binding on Guinea Pig Lung Membranes;
3. [$^3$H]LTD4 Receptor Binding on Human Lung Membranes;
4. In Vitro Guinea Pig Trachea; and
5. In Vivo Assays in Anesthetized Guinea Pigs.

The above assays are described by T. R. Jones et al., *Can. J. Physiol. Pharmacol.* 1991,69,1847–1854.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyzer, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post sensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an ED$_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene D$_4$ (LTD$_4$) or *Ascaris suum* antigen; 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., *Prostaglandins*, 28, 173–182 (1984) and McFarlane, C. S. et al., *Agents Actions*, 22, 63–68 (1987).)

Prevention of Induced Bronchoconstriction in Allergic Sheep

A. Rationale: Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods: Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.); and b) they have previously responded to inhalation challenge with *Ascaris suum* with both an acute bronchoconstriction and a late bronchial obstruction (W. M. Abraham et al., *Am. Rev. Resp. Dis.*, 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medicalnebulizer (Raindrop®, Puritan Bennett), which produces an aerosol with a mass median aerodynamic diameter of 6.2 mM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is conected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challenge. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

The invention will now be illustrated by the following non-limiting examples in which, unless stated otherwise:

(i) all operations were carried out at room or ambient temperature, that is, at a temperature in the range 18–25° C.;

(ii) evaporation of solvent was carried out using a rotary evaporator under reduced pressure (600–4000 pascals: 4.5–30 mm Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry, or microanalytical data;

(vi) yields are given for illustration only;

(vii) when given, NMR data are in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used: v (volume), w (weight), b.p. (boiling point), m.p. (melting point), L (liter(s)), mL (milliliters), g (gram(s)), mg (milligram(s)), mol (moles), mmol (millimoles), eq. (equivalent(s)).

EXAMPLE 1

(R, R or S)-1-[((1-]3-(2-(7-chloro-2-quinolinyl)-(E)-ethenyl)phenyl[-3-(2-(2-hydroxy-2-propionic acid)phenyl)-propyl)thio)methyl]cyclopropane acetic acid Diastereomeric Mixture Step 1 Methyl (R, R or S)-1[((1-[3-(2-(7-chloro-2-quinolinyl)-(E)-ethenyl)phenyl}-3(2-(2-hydroxy-2-propionaldehyde)phenyl)-propyl)thio)methyl]cyclopropane acetate To a mixture of oxalyl chloride (0.045 mmole, 4.3 ml) in $CH_2Cl_2$ (200 mL) at −60∞C was added DMSO (0.097 mmole, 7 ml) dropwise and was stirred 5 minutes. Then methyl (R,R or S)-1-[((1-[3-(2-(7-chloro-2-quinolinyl)-(E)-ethenyl)phenyl]-3-(2-(1,2-dihydroxy-1-methylethyl)-phenyl)propyl)thio)methyl]cyclopropaneacetate (*J. Org. Chem.*, 1996, 61, 8518–8525) (0.041 mole, 25 mg) in $CH_2Cl_2$ (50 mL) was added slowly at −60∞C. The reaction mixture was stirred for 15 minutes, and was quenched with $Et_3N$ (0.2 mmole, 28 ml). The temperature was raised to 25∞C, and $H_2O$ (2 mL) was added and the reaction mixture was extracted with EtOAc (2 mL). The organic extracts were dried over $Na_2SO_4$ and evaporated to dryness. The residue was pumped under high vacuum to constant weight and yielded 20 mg of the title compound which was used as such in the next step. $^1H$ NMR ($CD_3COCD_3$) d 0.38–0.53 (m, 4H), 1.51 (s, 3H), 2.05–2.30 (m, 2H), 2.39 (d, 1H), 2.46 (d, 1H), 2.55 (s, 2H), 2.60–2.80 (m, 2H), 3.05–3.15 (m, 1H), 3.58 (s, 3H), 4.05 (t, 1H), 7.15–7.30 (m, 3H), 7.39–7.55 (m, 5H) 7.62 (m, 1H), 7.75 (s, 1H), 7.85 (d, 1H), 7.9 (m, 2H), 8.0 (s, 1H), 8.35 (d, 1H), 9.62 (s, 1H).

Step 2 (R, R or S)-1-[((1-[3-(2-(7-chloro-2-quinolinyl)-(E)-ethenyl)phenyl]-3-(2-(2-hydroxy-2-propionic acid)phenyl)-propyl)thio)methyl]cyclopropane acetic acid To a solution of the aldehyde from Step 1 (20 mg, 0.032 mmol,) in EtOH (500 mL) and $AgNO_3$ (13 mg, 0.076 mmol) (predissolved in 30 ml $H_2O$) was added a KOH solution (0.16 mmol, 0.16 ml) dropwise. The reaction mixture was stirred at room temperature overnight. The reaction was acidified with acetic acid (10 ml) and diluted with $NH_4Cl$ saturated solution (2 mL) and extracted with EtOAc (2 mL). The organic extracts were dried over $Na_2SO_4$ and evaporated. The residue was purified by flash chromatography on silica gel using 4:8:1 $MeOH/CHCl_3/NH_3$ to yield 5 mg that was further purified by HPLC using Novapak silica column at 350 nm with $MeOH/H_2O/AcOH$ (80-20-0.1%) producing 2.8 mg of the title compound. $^1H$ NMR ($CD_3COCD_3$) d 0.35–0.68, (m, 4H), 1.75 (s, 3H), 2.10–2.25 (m, 2H), 2.45 (d, 2H), 2.50–2.70 (m, 3H), 3.0 (m, 1H), 4.05 (m, 1H), 7.05–7.20 (m, 3H), 7.35–7.55 (m, 5H), 7.6 (s, 1H), 7.8 (s, 1H), 7.85–8.0 (m, 3H), 8.02 (s, 1H), 8.25 (d, 1H). HRMS (FAB) m/z calc'd for $C_{35}H_{34}C_1NO_5S$: 616.192448 found 616.19269.

EXAMPLE 2

(R, R or S)-1-[((1-[3-(2-(7-chloro-2-quinolinyl)-{E}-ethenyl)phenyl]-3-(2-(2hydroxy-2-propionic acid)phenyl)-propyl)thio)methyl]cyclopropane acetic acid Major Isomer Step 1 (S)-2-(3-[3-(2-(7-chloro-2-quinolinyl)-(E)-ethenyl) phenyl]-3-tert butyldimethylsilyloxypropyl)ethanone To [S-(E)]-1-[2-[3-[3-[2-(7-Chloro-2-quinolinyl) ethenyl]-phenyl]-3-hydroxypropyl]phenyl]ethanone (*J.Org. Chem.*, 1993, 58, 3731–3735) (13.4 g, 30.35 mmol) in $CH_2Cl_2$ (67 mL) was added 2,6 lutidine (5.32 mL, 45.52 mmol). The mixture was cooled to −78∞C, then TBDMSO Tf (7.0 mL, 30.35 mmol) was added dropwise. The reaction was stirred 1 hour. The mixture was quenched by adding 25% $NH_4OAc$ solution (50 mL) and extracted with EtOAc (100 mL). The organic extract was dried over $Na_2SO_4$ and evaporated to a residue. The crude was purified by flash chromatography on silica using 95:5 hexane/EtOAc as eluant to yield 14.4 g of the title compound. $^1H$ NMR (CD3COCD3) d 0.15 (s, 6H), 0.95 (s, 9H), 2.0 (M, 2H), 2.81–3.02 (M, 2H), 4.95 (t, 1H), 7.25 (t, 2H), 7.36–7.55 (m, 5H), 7.72 (d, 1H), 7.75 (s, 2H), 7.82 (d, 1H), 7.90 (d, 2H), 8.0 (s, 1H), 8.35 (d, 1H).

Step 2 (S)-2-(3-[3-(2-(7-chloro-2-quinolinyl)-(E)-ethenyl) phenyl]-3-tert butyldimethylsilyloxypropyl) benzoylformaldehyde To predissolved $SeO_2$ (2.95 g, 26.57 mmol) in dioxane/$H_2O$ mixture (100 mL:0.48 mL) at 60∞C, was added the ketone from Step 1 (14.4 g, 26 mmol) in solution in dioxane (70 mL). The reaction mixture was heated at 100∞C overnight. The reaction was cooled to room temperature and filtered through a pad of celite and washed with dioxane (20 mL). Evaporation to dryness yielded the title compound which was used as such in the next step (Crude weight 14 g).

Step 3 (S)-2-(3-[3-(2-(7-chloro-2-quinolinyl)-(E)-ethenyl) phenyl]-3-tert butyldimethylsilyloxypropyl)benzoylformic acid To a solution of the aldehyde from Step 2 (14 g, 24.6 mmol) in EtOH (118 mL) was added a solution of $AgNO_3$ (10 g, 59 mmol) predissolved in $H_2O$ (23 mL) followed by a solution of KOH (118 mL, 118 mmol of 1M) dropwise. The mixture was stirred at room temperature overnight. The bulk of the EtOH was removed by evaporation, the aqueous was acidified with 1N HCl (118 mL) and extracted with EtOAc twice (100 mL). The organic extracts were dried over $Na_2SO_4$ and evaporated. The residue was purified by flash chromatography first with pure EtOAc then using 95:5 EtOAc: AcOH, to yield 5.0 g of the title compound. $^1H$ NMR ($CD_3COCD_3$) d 0.15 (s, 6H), 0.95 (s, 9H), 2.0 (m, 2H), 2.95–3.18 (m, 2H), 4.95 (t, 1H), 7.35–7.65 (m, 8H), 7.75–7.97 (m, 5H), 8.0 (s, 1H), 8.32 (d, 1H).

Step 4 8-Phenylmenthyl (S)-2-(3-[3-(2-(7-chloro-2-quinolyl)-(E)-ethenyl)phenyl]-3-terbutyldimethylsilyloxypropyl)benzoylformate To the keto acid from Step 3 (5.0 g, 8.5 mmol) in $CH_2Cl_2$ (40 mL) at 0∞C was added DMF (100 ml), followed by oxalyl chloride (1.12 ml, 12.8 mmol) dropwise. The reaction mixture was stirred for 1 hour. The reaction was evaporated to dryness and the residue was pumped under high vacuum for 1 hour and was used as such in the next step.

To 8-phenylmenthol (2.0 g, 8.6 mmol) in toluene (40 mL) and pyridine (0.7 mL, 8.5 mmol) was added the crude acid chloride from the previous step in toluene (10 mL) at room temperature). The mixture was stirred overnight. The reaction was quenched by adding $NH_4Cl$ saturated solution and HCl 1N 1:1 (50 mL) and was extracted with EtOAc twice (50 mL). The organic extracts were dried over $Na_2SO_4$ and evaporated to dryness: The residue was purified by flash chromatography with 99/1 toluene/EtOAc to give 5.0 g of the title compound. $^1H$ NMR ($CD_3COCD_3$) d 0.18 (s, 6H), 0.8–0.9 (m, 4H), 0.95 (s, 9H), 1.02–1.20 (m, 2H), 1.3 (d, 6H), 1.45–1.60 (m, 3H), 1.95–2.15 (m, 4H), 2.92–3.15 (m, 2H), 4.95 (t, 1H), 6.95 (t, 1H), 7.1–7.18 (m, 4H), 7.4–7.55 (m, 6H), 7.57–7.75 (m, 4H), 7.8–7.85 (m, 1H), 7.9–7.98 (d, d, 2H), 8.02 (s, 1H), 8.35 (d 1H).

Step 5 (S, R or S) 8-Phenylmenthyl-2-(3-[3-(2-(7-chloro-2 quinolyl-(E)-ethenyl)phenyl]-3-tertbutyldimethyl silyloxypropyl)-2-hydroxy-2-phenyl propionate To the keto-ester from Step 4, (1.0 g, 1.25 mmol in ether (25 mL)) was added at −78∞C MeMgBr 3M (0.83 mL, 2.5 mmol). The reaction mixture was stirred for 1.5 hours. The reaction was quenched by adding 0.4 mL AcOH directly into the mixture, followed by saturated $NH_4Cl$ solution (10 mL) and extracted with EtOAc (20 mL). The organic extracts were dried over $Na_2SO_4$ and evaporated to dryness. The residue was purified by flash chromatography using 90/10 hexane/EtOAc to give 0.8 g of the title compound. $^1$H NMR (CD$_3$COCD$_3$) d 0.2 (s, 6H), 0.62–1.2 (m, 23H), 1.35 (m, 2H), 1.72 (t, 1H), 1.80 (s, 3H), 2.70 (t, 1H), 2.85 (t, 1H), 4.75 (m, 1H), 5.0 (m, 1H), 7.05–7.25 (m, 8H), 7.35–7.55 (m, 5H), 7.65 (s, 1H), 7.75–8.05 (m, 5H), 8.35 (d, 1H).

Step 6 (S, R or S) 8-Phenylmenthyl-2-(3-[3-(2-(7-chloro-2 quinolyl-(E)-ethenyl)phenyl]-3-hydroxy)-2-hydroxy-2-phenyl propionate To the ester carbinol from Step 5 (0.8 g, 0.98 mmol) in THF was added TBAF solution (1 mL, 0.98 mmol) at room temperature overnight. The reaction was quenched with saturated NH$_4$Cl solution (10 mL) and extracted with EtOAc (2×10 mL). The organic extracts were dried over Na$_2$SO$_4$ and evaporated to dryness. The residue was purified by flash chromatography eluting with 95:5 CH$_2$Cl$_2$/acetone to give 0.39 g of a major isomer and 0.10 g of a minor isomer. Major: $^1$H NMR (CD$_3$COCD$_3$) d 0.65–1.00 (m, 9 H), 1.05 (s, 3H), 1.18 (m, 1H), 1.40 (m, 2H), 1.75 (m, 1H), 1.80 (s, 3H), 2.00 (m, 2H), 2.28 (m, 1H), 2.7 (m, 1H), 3.02 (m, 1H), 4.70 (m, 1H), 4.80 (m, 1H), 7.08–7.25 (m, 8H), 7.4–7.55 (m, 5H), 7.62 (m, 1H), 7.82–8.02 (m, 5H), 8.35 (d, 1H), Minor: 0.60–1.00 (m, 6H), 1.2 (m, 7H), 1.3–1.45 (m, 2H), 1.68 (s, 3H), 1.8–1.9 (m, 2H), 2.04 (m, 1H), 2.15–2.25 (m, 1H), 2.65–2.75 (m, 1H), 2.92–3.0 (m, 1H), 4.78–4.90 (m, 2H), 7.09–7.3 (m, 8H), 7.4–7.65 (m, 5H), 7.75–8.05 (m, 6H), 8.35 (d, 1H).

Step 7 (S, R or S) 8-Phenylmenthyl-2-(3-[3-(2-(7-chloro-2 quinolyl-(E)-ethenyl)phenyl]-3-methanesulfonate)-2-hydroxy-2-phenyl propionate To the major isomer of the alcohol carbinol ester from Step 6 (0.3 g, 0.41 mmol) in 1:1 toluene/CH$_3$CN (2.5 mL) was added Hünig's base (75 ml, 0.43 mmol). The reaction mixture was cooled to −40∞C and methanesulfonyl chloride (33 ml, 0.43 mmol) was added dropwise. The temperature was raised gradually to −30∞C over a period of 1 h. The reaction mixture was quenched by adding a saturated NaHCO$_3$ solution (3 mL) and extracted with EtOAc (3 mL). The organic extracts were dried over Na$_2$SO$_4$ and evaporated to dryness. The title compound thus obtained was used as such in the next step. $^1$H NMR (CD$_3$COCD$_3$) d 0.65–0.98 (m, 9H), 1.0 (s, 3H), 1.25–1.45 (m, 2H), 1.75 (m, 4H), 1.9 (m, 1H), 2.28 (m, 1H), 2.42–2.55 (m, 1H), 2.7–2.85 (m, 2H), 2.95–3.05 (m, 4H), 4.65–4.75 (m, H), 5.80 (t, 1H), 7.05–7.25 (m, 8H) 7.45–7.60 (m, 5H), 7.75–7.82 (d, 1H), 7.83–8.05 (m, 5H), 8.35 (d, 1H).

To degassed THF (1 mL) under N$_2$ was added 1-(mercaptomethyl)-1-cyclopropane acetic acid (*Bioorganic Med. Chem. Letters*, 1995, 5(3), 283–288) (60 mg, 0.41 mmol). To this solution, cooled to −15∞C, was added butyllithium (339 ml, 0.82 mmol). The temperature was raised to −8∞C for 30 minutes. Then the crude mesylate from the previous step (0.33 g, 0.41 mmol) dissolved in degassed THF (1 mL) was added to the reaction mixture dropwise. The mixture was stirred at 0∞C overnight. The reaction was quenched with saturated NH$_4$Cl solution (2 mL) and extracted with EtOAc (2 mL). The organic extracts were dried over Na$_2$SO$_4$ and evaporated to dryness. The residue was purified by flash chromatography using 1:1 hexane: EtOAc, adding 1% AcOH to give 138 mg of the title compound. $^1$H NMR (CD$_3$COCD$_3$) d 0.3–0.58 (m, 4H), 0.6–0.96 (m, 5H), 1.10–1.25 (m, 7H), 1.28–1.45 (m, 1H), 1.62 (s, 3H), 1.75–1.90 (m, 1H), 2.09–2.20 (m, 1H) 1H), 2.25–2.36 (m, 1H), 2.40–2.52 (m, 2H), 2.60 (s, 2H), 2.65–2.84 (m, 2H) 4.02 (t, 1H), 4.75 (m, 1H), 7.09 (m, 11H), 7.35–7.55 (3H), 7.62 (m, 1H), 7.75–8.05 (m, 4H), 8.35 (d, 1H).

Step 8 (R, R or S)-1-[((1-[3-(2-(7-chloro-2-quinolinyl)-{E}-ethenyl)phenyl]-3-(2-(2-hydroxy-2-propionic acid)phenyl)-propyl)thio)methyl]cyclopropane acetic acid To the carbinol ester from Step 7 (138 mg, 0.16 mmol) in EtOH (500 mL) was added 1N LiOH (480 mL, 0.48 mmol) solution. The reaction mixture was heated at reflux for 3 days, quenched with saturated NH$_4$Cl solution (2 mL) and acetic acid (30 mL), and extracted with EtOAc (2 mL). The organic extracts were dried over Na$_2$SO$_4$ and evaporated to dryness. The residue was purified by flash chromatography with 2/1 CHCl$_3$/MeOH as eluant first, then 2/1/0.25 CHCl$_3$/MeOH/NH$_4$OH giving 65 mg of the title compound which was further purified by an HPLC Novapak column, monitoring at 350 nm, with 80-20-0.1% MeOH—H2O—AcOH to give 11 mg of the title compound. $^1$H NMR (CD$_3$COCD$_3$) d 0.3–0.7 (m, 4H), 1.78 (d, 3H), 2.16–2.72 (m, 7H), 3.05 (t, 1H), 4.02 (t, 1H), 7.02–7.20 (m, 3H), 7.25–7.35 (m, 1H), 7.38–7.58 (m, 4H), 7.62 (t, 1H), 7.78 (d, 1H), 7.80–7.98 (m, 3H), 8.01 (s, 1H), 8.34 (d, 1H). $^{13}$C NMR (CD3COCD3) d 12.3, 12.3, 17.1, 27.5, 31.8, 39.2, 39.5, 39.6, 50.4, 76.0, 120.7, 125.8, 126.3, 126.2, 126.7, 127.1, 127.5, 128.1, 128.2, 129.0, 129.2, 129.2, 130.0, 131.2, 135.3, 135.8, 137.0, 137.5, 140.9, 141.7, 144.5, 149.1, 157.7, 173.1, 177.4. HRMS (FAB) m/z calc'd for C$_{35}$H$_{34}$ClN O$_5$S: 616.192448 found 616.19269.

EXAMPLE 3

(R, R or S)-1-[((1-[3-(2-(7-chloro-2-quinolinyl)-(E)-ethenyl)phenyl]-3-(2-(2-hydroxy-2-propionic acid)phenyl)-propyl)thio)methyl]cyclopropane acetic acid Minor Isomer Step 1 (S, R or S) 8-Phenylmenthyl-2-(3-[3-(2-(7-chloro-2 quinolyl-(E)-ethenyl)phenyl]-3-methanesulfonate)-2-hydroxy-2-phenyl propionate To the minor isomer of the alcohol carbinol ester from Example 2, Step 6 (0.5 g, 0.68 mmol) in 1:1 toluene/CH$_3$CN (4.0 mL) was added Hüinig's base (125 ml, 0.68 mmol). The reaction mixture was cooled to −40∞C. Then methanesulfonyl chloride (55 ml, 0.71 mmol) was added dropwise. The temperature was raised gradually to −30∞C over a period of 1 h. The reaction mixture was quenched by adding a saturated NaHCO$_3$ solution (3 mL) and extracted with EtOAc (3 mL). The organic extracts were dried over Na$_2$SO$_4$ and evaporated to dryness to give the title compound which was used as such in the next step. $^1$H NMR (CD$_3$COCD$_3$) d 0.65–0.98 (m, 9H), 1.0 (s, 3H), 1.25–1.45 (m, 2H), 1.75 (m, 4H), 1.9 (m, 1H), 2.28 (m, 1H), 2.42–2.55 (m, 1H), 2.7–2.85 (m, 2H), 2.95–3.05 (m, 4H), 4.65–4.75 (m, H), 5.80 (t, 1H), 7.05–7.25 (m, 8H) 7.45–7.60 (m, 5H), 7.75–7.82 (d, 1H), 7.83–8.05 (m, 5H), 8.35 (d, 1H).

To degassed THF (1 mL) under N$_2$ was added 1-(mercaptomethyl)-1-cyclopropane acetic acid (*Bioorganic Med. Chem. Letters*, 1995, 5(3), 283–288) (99 mg, 0.68 mmol). To this solution, cooled to −15∞C, was added butyllithium (542 ml, 1.36 mmol). The temperature was raised to −8∞C for 30 minutes. Then the crude mesylate from the previous step (0.55 g, 0.68 mmol) dissolved in degassed THF (1.6 mL) was added to the reaction mixture dropwise. The mixture was stirred at 0∞C overnight. The reaction was quenched with saturated NH$_4$Cl solution (2 mL) and extracted with EtOAc (2 mL). The organic extracts were dried over Na$_2$SO$_4$ and evaporated to dryness. The residue was purified by flash chromatography using 1:1 hexane: EtOAc, adding 1% AcOH to give 200 mg of the title compound. $^1$H NMR (CD$_3$COCD$_3$) d 0.3–0.58 (m, 4H), 0.6–0.96 (m, 5H), 1.10–1.25 (m, 7H), 1.28–1.45 (m, 1H), 1.62 (s, 3H), 1.75–1.90 (m, 1H), 2.09–2.20 (m, 1H), 2.25–2.36 (m, 1H), 2.40–2.52 (m, 2H), 2.60 (s, 2H), 2.65–2.84 (m, 2H) 4.02 (t, 1H), 4.75 (m, 1H), 7.09 (m, 11H), 7.35–7.55 (3H), 7.62 (m, 1H), 7.75–8.05 (m, 4H), 8.35 (d, 1H).

Step 2 (R, R or S)-1-[((1-[3-(2-(7-chloro-2-quinolinyl)-(E)-ethenyl)phenyl]-3-(2-(2-hydroxy-2-propionic acid)phenyl)-propyl)thio)methyl]cyclopropane acetic acid To the carbinol ester from Step 7 (200 mg, 0.23 mmol) in EtOH (500 mL) was added 1N LiOH (700 mL, 0.70 mmol) solution. The reaction mixture was heated at reflux for 3 days, quenched with saturated $NH_4Cl$ solution (2 mL) and acetic acid (30 mL), and extracted with EtOAc (2 mL). The organic extracts were dried over $Na_2SO_4$ and evaporated to dryness. The residue was purified by flash chromatography with 2/1 $CHCl_3$/MeOH as eluant first, then 2/1/0.25 $CHCl_3$/MeOH/$NH_4OH$, giving 80 mg of the title compound which was further purified by an HPLC Novapak column, monitoring at 350 nm, with 80-20-0.1% MeOH—$H_2O$—AcOH to give 13 mg of the title compound. $^1H$ NMR ($CD_3COCD_3$) d 0.3–0.7 (m, 4H), 1.78 (d, 3H), 2.16–2.72 (m, 8H), 3.05 (t, 1H), 4.02 (t, 1H), 7.02–7.20 (m, 3H), 7.25–7.35 (m, 1H), 7.38–7.58 (m, 4H), 7.62 (t, 1H), 7.78 (d, 1H), 7.80–7.98 (m, 3H), 8.01 (s, 1H), 8.34 (d, 1H). HRMS (FAB) m/z calc'd for $C_{35}H_{34}ClNO_5$: 616.192448 found 616.19269.

EXAMPLE 4

Isolation of 1-[((1-[3-(2-(7-chloro-2-quinolinyl)-(E)-ethenyl)phenyl]-3-(2-(2-hydroxy-2-propionic acid)phenyl) propyl)thio)methyl]-cyclopropane acetic acid from human bile To healthy subjects were administered a single oral dose of 50 mg montelukast sodium after an overnight fast (3 subjects) or 5 hr after a fatty mean (3 subjects). Bile was collected through an oro-gastroduodenal tube placed near the ampulla of vater, from 2–8 hr or 8–12 hr postdose. Two hours before the end of the collection procedure cholecystokinin C-terminal octapeptide was administered intravenously to stimulate gall bladder contractions and hence enhance the bile flow. Subjects were fasted throughout the collection procedure. All samples were stored at −70° C. in the dark until analysis, and all analyses were performed under amber light conditions.

Bile samples were analyzed directly after centrifugation using a Beckman C18 column (4.6×250 mm) eluted at 1.1 ml/min with linear gradients from 35% to 45% acetonitrile in 1 mM ammonium acetate, pH 3.5 in 5 min, 45% to 55% acetonitrile in 35 min, 55% to 87% acetonitrile in 20 min, 87% to 95% acetonitrile in 0.3 min. Under these HPLC conditions, the title compound eluted at about 53 min. as diastereomeric mixture. The title compound thus obtained was repurified using a Zorbax-XDB Eclipse C8 column (4.6×250 mm), eluted with a 15-min linear gradient from 28% acetonitrile and 28% methanol in water to 47% acetonitrile and 47% methanol in water. The retention time of the title compound under these conditions was about 15 min. The NMR and MS spectra of the repurified compound were consistent with those obtained from an authentic sample of the title compound.

What is claimed is:

1. A compound of the formula

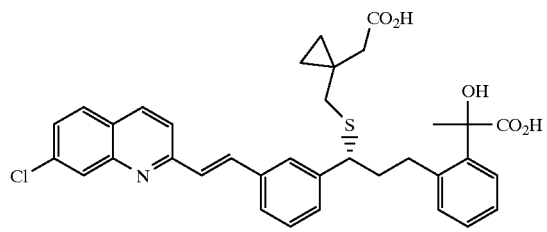

and the individual optical isomers thereof, or a pharmaceutically acceptable derivative thereof.

2. A pharmaceutical composition comprising a thereapeutically effective amount of a compound of claim 1 and a pharmaceutically acceptable carrier.

3. A method of preventing the actions of leukotriene in a mammal comprising administering to said mammal in need of such treatment a therapeutically effective amount of a compound of claim 1.

4. A method for the treatment or prevention of asthma, allergies or inflammation in a mammal comprising administering to said mammal in need of such treatment a therapeutically effective amount of a compound of claim 1.

5. A process for the preparation of a compound of claim 1 which comprises:

a) reacting a compound of formula 1

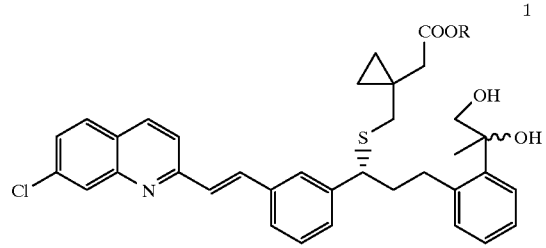

wherein R is lower alkyl with dimethylsulfoxide and an electrophile to provide a compound of formula 2;

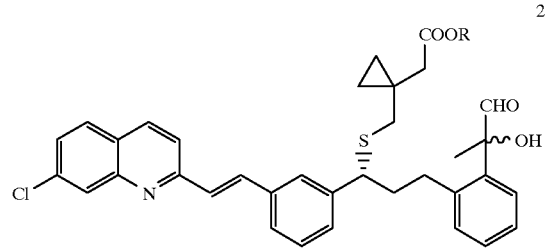

b) reacting a compound of formula 2 with silver nitrate and a base to provide the compound of claim 1.

6. A process for the preparation of the individual diastereomers of a compound of claim 1 which comprises:

(a) separating a diastereomeric mixture of a compound of formula 7:

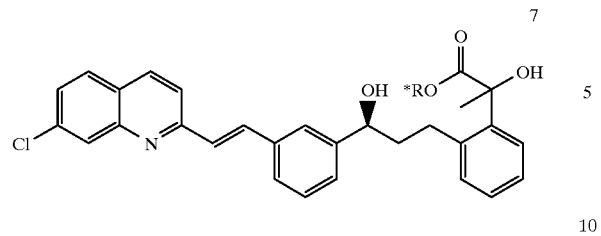
wherein R* is 8-phenylmenthyl;
(b) reacting an individual diastereomer with methanesulfonyl chloride to provide the corresponding mesylate;
(c) reacting the mesylate from step (b) with the dianion of 1-mercaptomethylcyclopropaneacetic acid to provide a compound of formula 8:
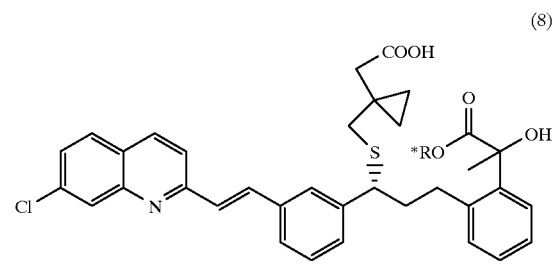
(d) removing the 8-phenylmenthyl group to provide a compound of claim 1.
* * * * *